US012343012B2

(12) United States Patent
Liu et al.

(10) Patent No.: US 12,343,012 B2
(45) Date of Patent: Jul. 1, 2025

(54) SURGICAL STAPLER AND A CONTROL METHOD THEREFOR

(71) Applicant: B. J. ZH. F. PANTHER MEDICAL EQUIPMENT CO., LTD., Beijing (CN)

(72) Inventors: Qing Liu, Beijing (CN); Xiaoqiang Chen, Beijing (CN); Xuelan Yang, Beijing (CN); Libo Liu, Beijing (CN)

(73) Assignee: B. J. ZH. F. PANTHER MEDICAL EQUIPMENT CO., LTD., Beijing (CN)

( * ) Notice: Subject to any disclaimer, the term of this patent is extended or adjusted under 35 U.S.C. 154(b) by 0 days.

(21) Appl. No.: 18/690,475

(22) PCT Filed: Sep. 8, 2022

(86) PCT No.: PCT/CN2022/117913
§ 371 (c)(1),
(2) Date: Mar. 8, 2024

(87) PCT Pub. No.: WO2023/036263
PCT Pub. Date: Mar. 16, 2023

(65) Prior Publication Data
US 2024/0237981 A1    Jul. 18, 2024

(30) Foreign Application Priority Data

Sep. 10, 2021   (CN) ............................ 202110626 46.9
Sep. 18, 2021   (CN) .......................... 202111098001.0

(51) Int. Cl.
*A61B 17/072*     (2006.01)
*A61B 17/00*      (2006.01)

(52) U.S. Cl.
CPC .. *A61B 17/072* (2013.01); *A61B 2017/00022* (2013.01); *A61B 2017/00128* (2013.01);
(Continued)

(58) Field of Classification Search
CPC . A61B 90/98; A61B 17/115; A61B 17/07207; A61B 2017/00725;
(Continued)

(56) References Cited

U.S. PATENT DOCUMENTS 9,913,642 B2 *   3/2018   Leimbach ............ A61B 17/072
10,760,932 B2 *  9/2020   Zemlok ............ A61B 17/07207

FOREIGN PATENT DOCUMENTS

CN    104042293 A    9/2014
CN    104224255 A    12/2014
(Continued)

OTHER PUBLICATIONS

First Office Action issued in Chinese Patent Application No. 202111098001.0; mailed Dec. 28, 2022; 11 pgs.
(Continued)

*Primary Examiner* — Nathaniel C Chukwurah
(74) *Attorney, Agent, or Firm* — HAUPTMAN HAM, LLP

(57) ABSTRACT

A surgical stapler and a control method therefor. A control part of the surgical stapler is used to acquire a real-time drive current value and a jump current average value of a drive part; then, determine the difference value between the drive current value at a current moment and the drive current value at a previous moment; compare the difference value to the jump current average value, if the difference value is greater than the jump current average value, control the drive part to stop working. Thus, an operator does not have to determine by his or herself whether anastomosis action is completed before operating the surgical stapler, thereby increasing surgical efficiency.

14 Claims, 4 Drawing Sheets

(52) U.S. Cl.
CPC ............... *A61B 2017/00398* (2013.01); *A61B 2017/00734* (2013.01)

(58) Field of Classification Search
CPC .. A61B 2017/00123; A61B 2090/0803; A61B 2017/07214; A61B 2017/00473; A61B 2017/00398; A61B 2017/00128; A61B 2017/00017; A61B 2017/00022; A61B 2017/00734; A61B 2017/00119; Y02E 60/10
See application file for complete search history.

(56) References Cited

FOREIGN PATENT DOCUMENTS

| | | |
|---|---|---|
| CN | 110192903 A | 9/2019 |
| CN | 113907823 A | 1/2022 |

OTHER PUBLICATIONS

International Search Report and Written Opinion issued in International Patent Application No. PCT/CN2022/117913; mailed Nov. 28, 2022; 16 pgs.

* cited by examiner

SURGICAL STAPLER AND A CONTROL METHOD THEREFOR

RELATED APPLICATIONS

The present application is a U.S. National Phase of International Application Number PCT/CN2022/117913 filed Sep. 8, 2022, which claims priority to Chinese Application Numbers CN202111062646.9 filed Sep. 10, 2021, and CN202111098001.0 filed Sep. 18, 2021.

TECHNICAL FIELD

The present invention relates to the field of medical devices, and in particular, to a surgical stapler and a control method thereof.

BACKGROUND

A surgical stapler is a device for medical replacement of manual suturing. The surgical stapler is generally provided with structures such as a staple cartridge assembly and a cutting knife. During surgery, a tissue to be stapled is clamped and snapped into a jaw of a staple cartridge assembly, a handle of an instrument compartment is pressed to drive a cutting knife to dissociate the tissue, and at the same time, staples provided in the staple cartridge assembly are pushed out and molded to staple the tissue. However, in the prior art, the operator operates the surgical stapler after judging whether or not the stapling operation is completed, thereby affecting the progress and efficiency of the procedure.

SUMMARY

In view of this, embodiments of the present invention provide a surgical stapler and a control method therefor, so as to solve the problem in the prior art that an operator performs an operation on the surgical stapler after determining whether an anastomosis action is completed, thereby affecting the progress and efficiency of a surgery.

According to a first aspect, an embodiment of the present invention provides a surgical stapler, comprising a housing, a control part and a drive part for providing power are provided in the housing, and the control part is electrically connected to the drive part;

the control part is configured to acquire a real-time drive current value and a jump current average value of the drive part; determining a difference value between a drive current value at a current moment and a drive current value at a previous moment; and comparing the difference value with a jump current average value, and if the difference value is greater than the jump current average value, controlling the drive part to stop working.

Specifically, the control part is further configured to acquire a historical drive current value of the drive part, determining a difference value between the drive current values at two adjacent moments; and determining the jump current average value according to all the difference values.

Specifically, the control part is further configured to compare the real-time drive current value with a drive current threshold value, and when the real-time drive current value is greater than or equal to the drive current threshold value, control the drive part to stop working.

Specifically, the surgical stapler further comprises a transmission part and a firing lever, the drive part is connected to one end of the firing lever through the transmission part; the control part is electrically connected to the drive part;

the control part is used for controlling, when the surgical stapler is activated, the drive part to drive the firing lever through the transmission part to perform a reset calibration action.

Specifically, the surgical stapler further comprises a load switch and a detachable staple cartridge assembly; the control part is electrically connected to the load switch;

when the staple cartridge assembly is installed, the staple cartridge assembly triggers the load switch;

the control part is used for recording a trigger time of the load switch, and comparing the trigger time with a time threshold value, and if the trigger time is greater than or equal to the time threshold value, determining that the staple cartridge assembly is loaded successfully.

Specifically, the control part is further configured to compare the real-time drive current value with a preset variable current value, when the real-time drive current value is greater than the preset variable current value, controlling the drive part to drive the firing lever to continue to move in a direction away from the drive part via the transmission part, so as to increase the closing stroke of the staple cartridge assembly and reduce the rotation speed of the drive part, so as to increase the tissue positioning capability of the staple cartridge assembly.

Specifically, the control part is further used for controlling the drive part to drive the firing lever through the transmission part to perform a reset calibration action when the staple cartridge assembly is removed.

Specifically, the surgical stapler further comprises a sense part disposed in the housing; the transmission part is provided with a protrusion, the sensing area of the sense part is located on a moving path of the protrusion on the transmission part, and the control part is electrically connected to the sense part;

the control part is used for controlling, when the surgical stapler is activated or the staple cartridge assembly is removed, the drive part to drive the firing lever to move in a direction close to the drive part via the transmission part, so that the sense part senses the protrusion for the first time;

when the sense part senses the protrusion for the first time, the drive part is controlled to drive the firing lever to move in a direction away from the drive part via the transmission part, so that the protrusion is detached from the sensing area of the sense part;

when the sensing area of the sense part is detached, controlling the drive part to drive the firing lever to move in a direction close to the drive part via the transmission part, so that the sense part senses the protrusion for a second time;

controlling the drive part to stop working when the sense part senses the protrusion for the second time.

Specifically, the surgical stapler further comprising a detachable power supply and a battery circuit board disposed inside the housing, the control part is electrically connected to the battery circuit board;

and the control part is configured to, when the power supply is installed, collect a voltage on the battery circuit board, determine whether the voltage is an operating voltage, and if the voltage is an operating voltage, determine that the surgical stapler is activated.

Specifically, the surgical stapler further comprises an identification part electrically connected to the control part, and the staple cartridge assembly is further provided with an information identifier;

the identification part is configured to identify an information identifier on the cartridge assembly;

and the control part is configured to control the surgical stapler to be in the stopped state if the identification fails, and to control the surgical stapler to be in the activated state if the identification succeeds.

Specifically, the control part is further configured to record total identification times and total identification success times of the identification part, and obtain a preset correspondence between the total identification times and the total identification success times; determining a preset total identification success times according to the correspondence and the total identification times; and comparing the total identification success times with the preset total identification success times, and if the total identification success times is greater than or equal to the preset total identification success times, controlling the surgical stapler to be in a shutdown state.

Specifically, the identification part acquires an identification record of the information identifier on the staple cartridge assembly, and if the identification record is a successful identification record, then determining that the identification of the information identifier fails.

According to a second aspect, an embodiment of the present invention provides a method for controlling a surgical stapler, which is applied to the foregoing surgical stapler and comprising:

acquiring a real-time drive current value and a jump current average value of a drive part;

determining a difference value between a drive current value at a current moment and a drive current value at a previous moment;

comparing the difference value with a jump current average value, and if the difference value is greater than the jump current average value, controlling the drive part to stop working.

Further, the method further comprises:

when the retraction trigger link or the firing trigger link is triggered, the drive part drives the firing lever to retract or advance.

Provided are a surgical stapler and a control method therefor. The control part of the surgical stapler is used for acquiring a real-time drive current value and a jump current average value of a drive part; then, a difference value between the drive current value at a current moment and the drive current value at a previous moment is determined; then, the difference value is compared with the jump current average value, and if the difference value is greater than the jump current average value, the drive part is controlled to stop working. Thus, an operator does not have to determine by his or herself whether anastomosis action is completed before operating the surgical stapler, thereby increasing surgical efficiency.

BRIEF DESCRIPTION OF THE DRAWINGS

The following drawings of the invention are used herein as part of embodiments of the invention to understand the invention. Embodiments and descriptions of the invention are shown in the attached drawings to explain the principle of the invention.

In the drawings.

DESCRIPTION OF REFERENCE NUMERALS

1—power supply, 101—conduction sheet, 102—battery, 103—signal conduction sheet, 2—housing, 3—indication lamp, 4—drive part, 5—trigger, 6—identification part, 7—gear, 8—rack, 9—staple cartridge assembly, 10—information identifier, 11—protrusion, 12—firing trigger link, 13—retraction trigger link, 14—acknowledgement switch, 15—battery circuit board, 16—spring clip, 17—control part, 1701—processor, 1702—power supply management part, 1703—memory.

DETAILED DESCRIPTION

In the following description, numerous specific details are set forth in order to provide a more thorough understanding of the invention. It will be apparent, however, to one skilled in the art that the present invention may be practiced without one or more of these details. In other instances, to avoid obscuring the present invention, some technical features known to those of ordinary skill in the art are not described.

It should be noted that the terminology used herein is for the purpose of describing particular embodiments only and is not intended to be limiting of exemplary embodiments in accordance with this invention. As used herein, the singular forms ' a', ' an', and ' the' are intended to include the plural forms as well, unless the context clearly indicates otherwise. In addition, it should also be understood that the terms ' comprises' and/or 'comprising,' when used in this specification, specify the presence of stated features, integers, steps, operations, elements, and/or components, but do not preclude the presence or addition of one or more other features, integers, steps, operations, elements, components, and/or groups thereof.

Exemplary embodiments in accordance with the invention will now be described in more detail with reference to the accompanying drawings. However, these exemplary embodiments may be embodied in many different forms and should not be construed as limited to only the embodiments set forth herein. It should be appreciated that these embodiments are provided so that this disclosure will be thorough and complete, and will fully convey the concept of these exemplary embodiments to those of ordinary skill in the art.

Figure 1:
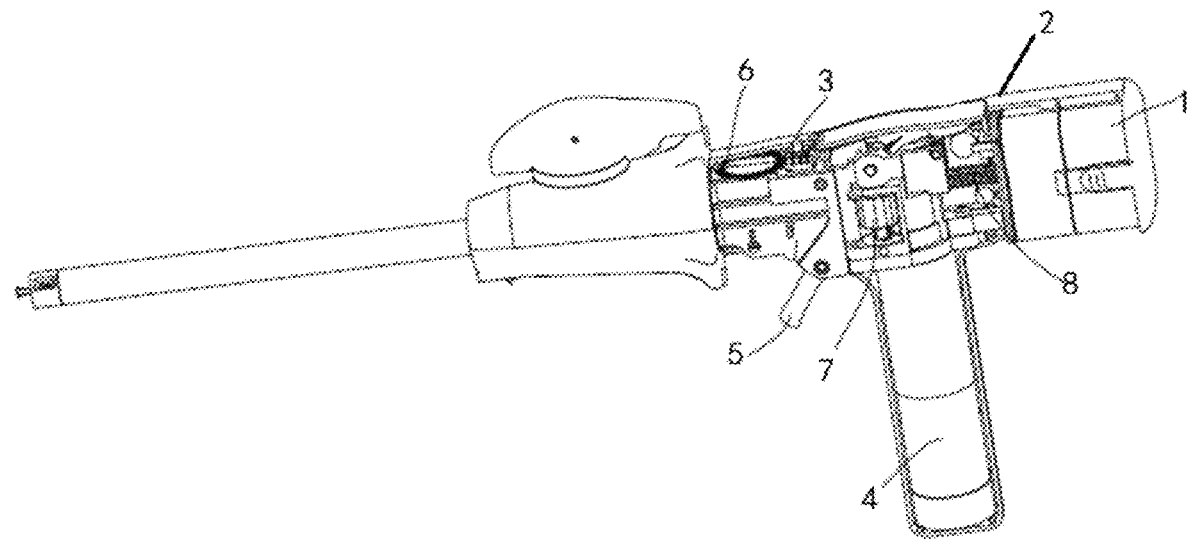
FIG. 1 is a partial cross-sectional diagram of a surgical stapler in accordance with an optional embodiment of the present invention.
Figure 6:
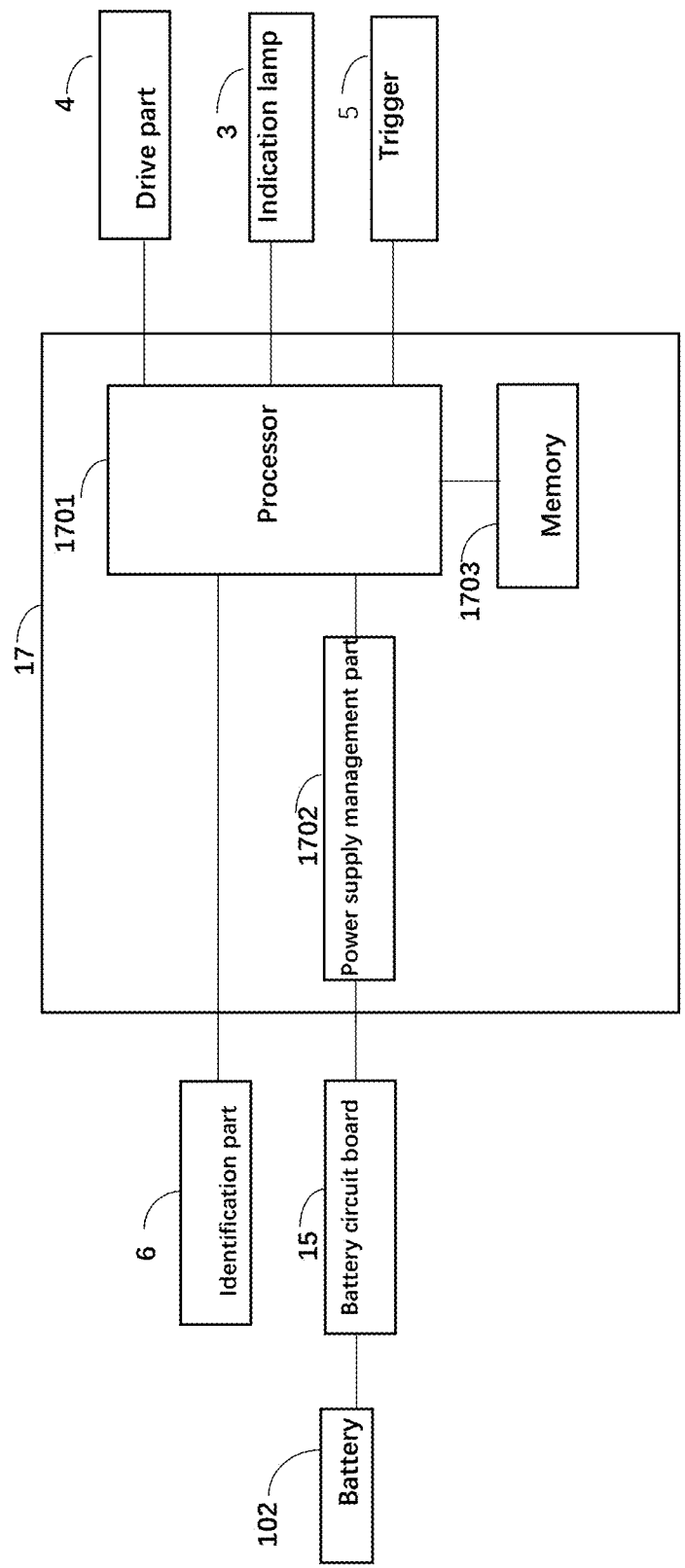
FIG. 6 is a schematic circuit diagram of a surgical stapler according to an optional embodiment of the present invention.

In a first aspect, as shown in FIGS. 1 and 6, an embodiment of the present invention provides a surgical stapler, comprising a housing 2, a control part 17 and a drive part 4 for providing power are provided in the housing 2, and the control part 17 is electrically connected to the drive part 4; the control part 17 is configured to acquire a real-time drive current value and a jump current average value of the drive part 4, and determine a difference value between a drive current value at a current moment and a drive current value at a previous moment. The difference value is compared with the jump current average value, and if the difference value is greater than the jump current average value, the drive part 4 is controlled to stop working.

The housing 2 is tubular as a whole, the housing 2 is provided with a handle shell formed by extending radially along the housing 2, and on the one hand, the handle shell can be conveniently held by an operator; On the other hand, the motor is disposed in the shell cavity formed by the handle shell, so that the space of the shell cavity of the shell 2 is effectively utilized, and the volume of the surgical stapler is reduced.

In this embodiment, the control part 17 of the surgical stapler is configured to acquire a real-time drive current value and a jump current average value of the drive part 4 (the acquiring ways include direct acquiring and conversion acquiring); then determine a difference value between the drive current value at the current moment and the drive current value at the previous moment; and then compare the difference value with the jump current average value, and if the difference value is greater than the jump current average value, control the drive part 4 to stop working. Thus, an operator does not have to determine by his or herself whether anastomosis action is completed before operating the surgical stapler, thereby increasing surgical efficiency.

Exemplarily, assuming that the drive current value at the current moment is 5 A, the drive current value at the previous moment is 4.5 A, and the jump current average value is 0.4 A, in this way, a difference value between the drive current value at the current moment and the drive current value at the previous moment is 0.5 A, and the difference value is greater than the jump current average value, it can be determined that the anastomosis action is completed, and in this way, the control part 17 controls the drive part 4 to stop working.

Further, in order to facilitate the operator in knowing the working state of the surgical stapler, the housing 2 is further provided with an indication lamp 3 electrically connected to the control part 17, and after the anastomosis action is completed, the control part 17 controls the indication lamp 3 to light up, so that the operator can determine, by using the indication light 3, whether the surgical stapler completes the anastomosis action.

The process of determining the jump current average value in the foregoing embodiment is described in detail in the following.

Specifically, the control part 17 is further configured to acquire a historical drive current value of the drive part 4, and determine a difference value between drive current values at two adjacent moments; determine the jump current average value based on all of the difference values.

The historical drive current value may be a drive current value during a period of time in the anastomosis operation process. After the historical drive current value of the drive part 4 is acquired, a difference value between the drive current values at two adjacent moments is determined, exemplarily, assuming that the drive current value at the first moment is 5 A, and the drive current value at the second moment is 4.6 A, the drive current value at the third moment is 4.3 A, and then the drive current difference value at the first moment and the second moment is 0.4 A, the difference value between the drive currents at the second time and the third time is 0.3 A, and so on, so as to obtain the difference value between the drive current values at all two adjacent moments. After all the difference values are obtained, the average value of all the difference values is calculated, and finally the jump current average value is determined.

In other embodiments, the control part 17 is further configured to compare the real-time drive current value with a drive current threshold value, and control the drive part 4 to stop working when the real-time drive current value is greater than or equal to the drive current threshold value.

In the process of the surgical stapler performing an anastomosis action, the control part 17 detects a drive current of the drive part 4 in real time, and if the real-time drive current value is greater than or equal to a drive current threshold value, the control part 17 controls the drive part 4 to stop working, thereby preventing the drive part 4 from being damaged due to an over-current working. The drive current threshold is a maximum current value of the drive part 4 in normal operation.

Specifically, in the above embodiment, the surgical stapler further comprises a transmission part and a firing lever, wherein the drive part 4 is connected to one end of the firing lever through the transmission part. The control part 17 is electrically connected to the drive part 4. The control part 17 is used for controlling, when the surgical stapler is activated, the drive part 4 to drive the firing lever through the transmission part to perform a reset calibration action.

The transmission part can use an existing transmission structure. Specifically, as shown in FIG. 1, the transmission part comprises a rack 8 and a gear 7, one end of the rack 8 is connected to the firing lever, the drive part 4 is an electric motor, a rotating shaft of the electric motor is coaxially connected to the gear 7, and the gear 7 is engaged with the rack 8 for transmission. The specific working principle of the transmission part is as follows: the rotation of the motor drives the gear 7 to rotate, thereby driving the rack 8 to make a linear reciprocating motion, and further driving the firing lever to make a linear reciprocating motion. In this way, the motor can drive the firing lever to move.

The forward rotation direction of the motor is a rotation direction in which the motor can drive the firing lever to move in a direction away from the motor, i. e. a protruding action, and the direction rotation direction of the motor is a rotation direction in which the motor can drive the firing lever to move in a direction close to the motor, i. e. a retraction action.

In the case where the surgical stapler is activated, the control part 17 controls the rotation direction of the transmission part, thus driving the transmission part to drive the firing lever to complete the reset calibration action, so as to avoid the reset shielding, thereby making the installation operation of the staple cartridge assembly 9 more smooth; Furthermore, there is no need to manually reset the firing lever, which facilitates the use of the surgical stapler.

Figure 2:
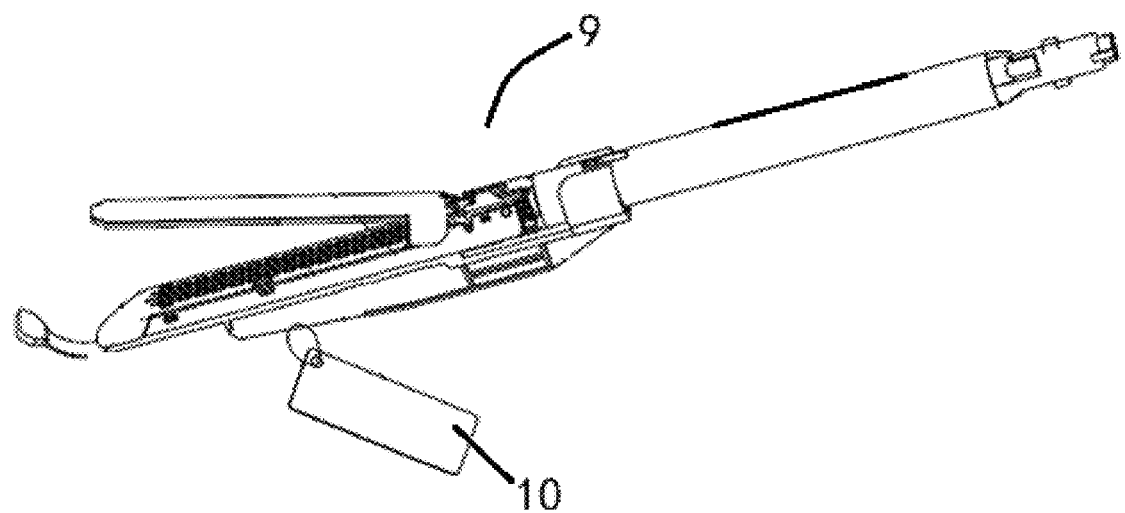
FIG. 2 is a structural diagram of a staple cartridge assembly in accordance with an optional embodiment of the present invention.

Further, as shown in FIGS. 2 and 6, the surgical stapler also comprises a load switch and a detachable staple cartridge assembly 9; the control part 17 is electrically connected to the load switch; when the staple cartridge assembly 9 is installed, the staple cartridge assembly 9 triggers the load switch; The control part 17 is used for recording the trigger time of the load switch, comparing the trigger time with a time threshold, and if the trigger time is greater than or equal to the time threshold, determining that the staple cartridge assembly 9 has been loaded successfully.

The staple cartridge assembly 9 may be an existing staple cartridge assembly 9, which is not strictly limited in this embodiment.

Specifically, the staple cartridge assembly 9 is detachably connected to the firing lever. When the staple cartridge assembly 9 is installed, that is to say, the staple cartridge assembly 9 is electrically connected to the firing lever, and the staple cartridge assembly 9 can trigger the load switch via the pushing part, the control part 17 records a trigger time of the load switch, compares the trigger time with a time threshold, and if the trigger time is greater than or equal to the time threshold, determining that the staple cartridge assembly 9 has been loaded successfully. Thereby automatically identifying whether the staple cartridge assembly 9 has been installed successfully. Further, if the trigger time is less than the time threshold value, the control part 17 may control the indication light 3 to illuminate, thereby reminding the operator to check the installation state of the staple cartridge assembly 9.

In some other embodiments, the control part 17 is further configured to compare the real-time drive current value with a preset variable current value, when the real-time drive current value is greater than the preset variable current value, the drive part 4 is controlled to drive the firing lever to continue to move in a direction away from the drive part 4 via the transmission part, so as to increase the closing stroke of the staple cartridge assembly 9 and reduce the rotation speed of the drive part 4, so as to increase the tissue positioning capability of the staple cartridge assembly 9.

During the anastomosis, the control part 17 detects the real-time drive current value of the drive motor, and when the real-time drive current value is greater than the preset variable current value, then it indicates that the tissue clamped by the surgical stapler is thick, and the control part 17 controls the drive part 4 to drive the firing lever to move in a direction away from the drive part 4 through the transmission part, so as to increase the closing stroke of the staple cartridge assembly 9, thereby achieving the purpose that the thick tissue can still completely close and hold the tissue, and the rotation speed of the drive part 4 is reduced, so as to increase the tissue positioning capability of the staple cartridge assembly 9, thereby achieving the purpose that thick tissues can still complete anastomosis. The preset variable current value may be set by an operator, which is not strictly limited in this embodiment.

In another lower embodiment, the control part 17 is also used for controlling the drive part 4 to drive the firing lever through the transmission part to perform a reset calibration action when the staple cartridge assembly 9 is removed.

After the staple cartridge assembly 9 is removed, that is, the staple cartridge assembly 9 is detached from the firing lever, the control part 17 controls the drive part 4 to drive the firing lever through the transmission part to perform a reset calibration action, thereby facilitating the next use of the surgical stapler.

The resetting calibration action in the above embodiment will be described in detail below.

Figure 3:
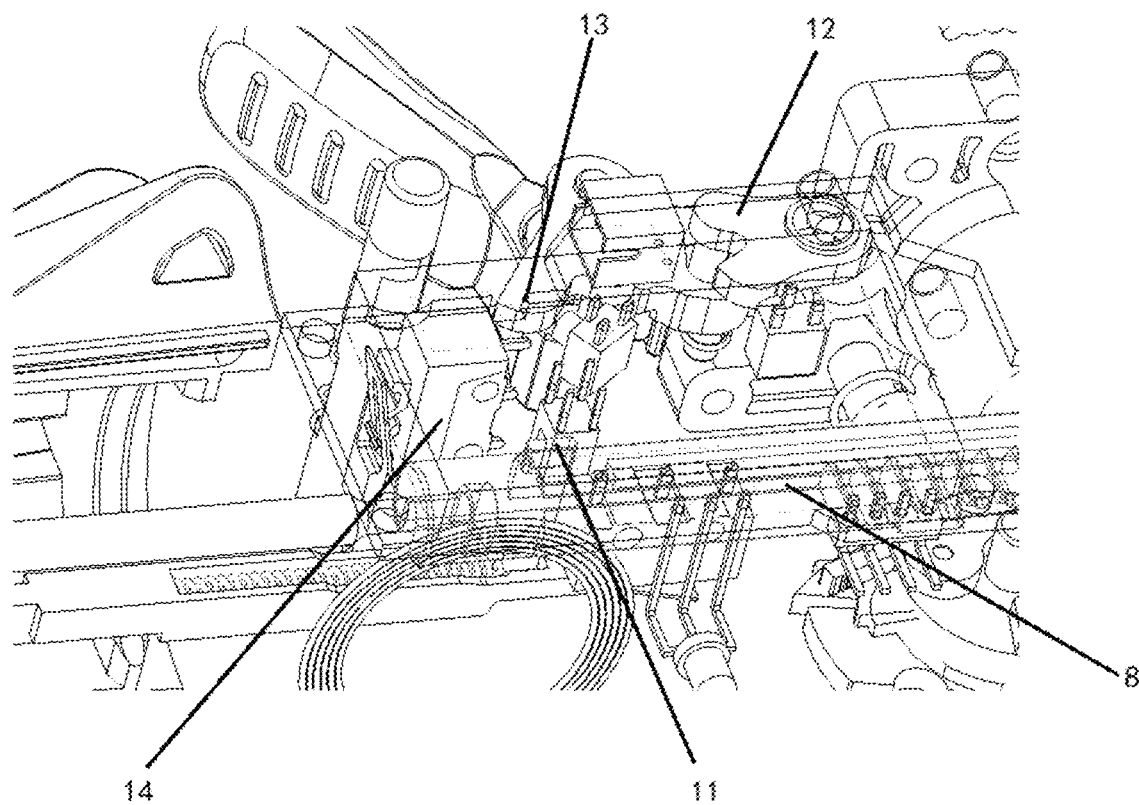
FIG. 3 is a structural diagram of a transmission part according to an optional embodiment of the present invention.

Specifically, as shown in FIGS. 1 and 3, the surgical stapler further comprises a sense part provided in the housing 2; the transmission part is provided with a protrusion 11, the sensing area of the sense part is located on a moving path of the protrusion 11 on the transmission part, and the control part 17 is electrically connected to the sense part;

the control part 17 is used for controlling the drive part 4 to drive the firing lever to move in a direction close to the drive part 4 via the transmission part so that the sense part senses the protrusion 11 for the first time, when the surgical stapler is activated or the staple cartridge assembly 9 is removed;

when the sense part senses the protrusion 11 for a first time, the drive part 4 is controlled to drive the firing lever to move in a direction away from the drive part 4 via the transmission part, so that the protrusion 11 is detached from the sensing area of the sense part;

when the sensing area of the sense part is detached, controlling the drive part 4 to drive the firing lever to move in a direction close to the drive part 4 via the transmission part, so that the sense part senses the protrusion 11 for a second time;

when the sense part senses the protrusion 11 for the second time, the drive part 4 is controlled to stop working.

The protrusion 11 may be disposed on the rack 8, the sense part may be a photoelectric sensing component. The protrusion 11 is located in a sensing area of the sense part, then it can be determined that the firing lever is located at an initial position, and in the present embodiment, the drive part 4 drives the rack 8 to retract, so that when the protrusion 11 is located in the sensing area for the first time, the drive part 4 drives the rack 8 to perform a protrude-retract action, until the protrusion 11 is located in the sensing area for the second time, so as to avoid blocking the zero position of the firing lever, thereby ensuring that the staple cartridge assembly 9 can be successfully installed.

In yet another embodiment, the surgical stapler further comprises a detachable power supply 1 and a battery circuit board 15 provided inside the housing 2, wherein the control part 17 is electrically connected to the battery circuit board 15; the control part 17 is configured to collect a voltage on the battery circuit board 15 when the power source 1 is installed, determine whether the voltage is a working voltage, and if the voltage is the working voltage, determine that the surgical stapler is activated.

Figure 4:
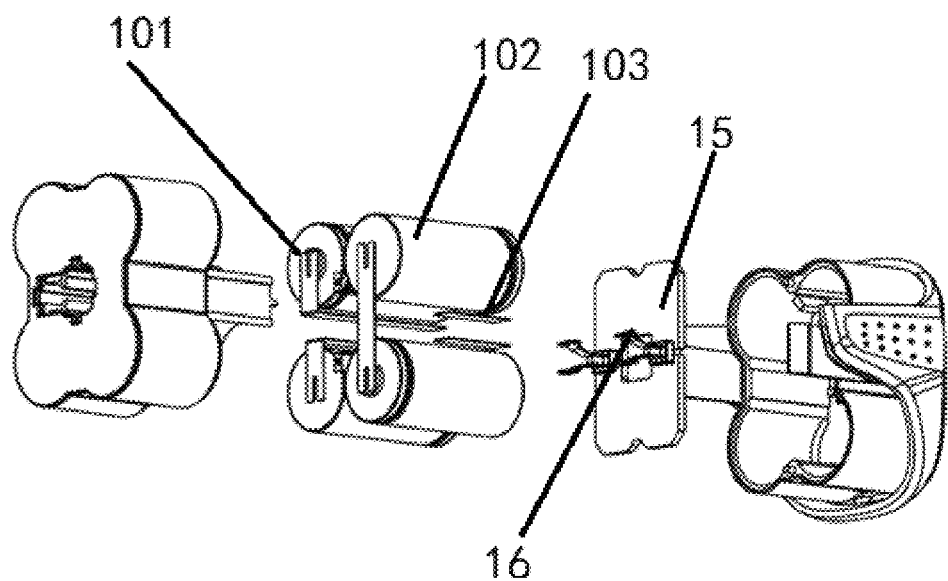
FIG. 4 is a structural diagram of a power supply according to an optional embodiment of the present invention.

As shown in FIG. 4, the power source 1 comprises a battery 102 and a conduction sheet 101 and a signal conduction sheet 103 disposed on the battery 102, and a spring clip 16 is disposed on the circuit board. After the power source 1 is installed, the battery 102 supplies power to each component through the conduction sheet 101, the battery circuit board 15 is connected to the battery 102 through the spring sheet 16, and the battery circuit board 15 communicates with each component through the signal conduction sheet 103.

In this embodiment, the control part 17 collects a voltage of the battery circuit board 15, and when it is determined that the voltage is a working voltage, may determine that the power source 1 is successfully installed, so as to determine that the surgical stapler is in an activated state and can be used by an operator. In this way, automatic identification of whether the power source 1 is successfully installed can be implemented, thereby facilitating the operator in using the surgical stapler. Likewise, after it is determined that the power source 1 is installed successfully, the control part 17 may further control the power source 1 to turn on the indication lamp 3, so that the operator can intuitively understand the installation situation of the power source 1.

Figure 5:
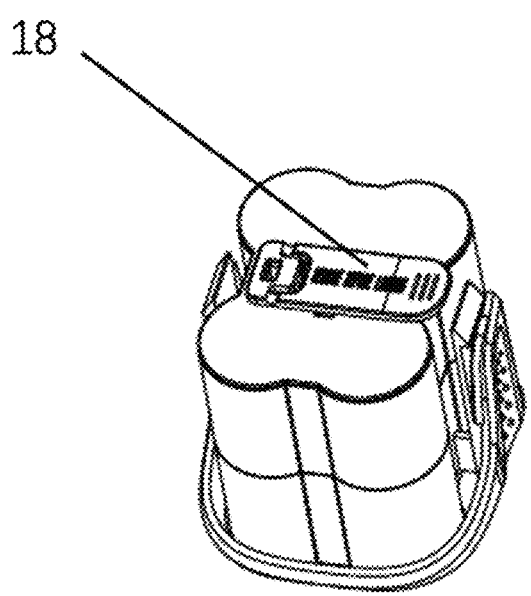
FIG. 5 is a structural diagram of a power supply and an insulating sheet according to the present invention.

Further, as shown in FIG. 5, the power supply 1 can further include an insulating sheet. When the surgical stapler is not used, the operator can plug the insulating sheet 18 between the spring clip 16 and the battery 102, so as to achieve the isolation effect, thereby reducing the power consumption of the battery 102.

In some other embodiments, the surgical stapler also comprises an identification part 6 electrically connected to the control part 17, and the staple cartridge assembly 9 is further provided with an information identifier 10; the identification part 6 is used for identifying an information identifier 10 on the staple cartridge assembly 9; and the control part 17 is used for controlling the surgical stapler to be in a stopped state if the identification fails, and controlling the surgical stapler to be in an activated state if the identification succeeds.

The identification part 6 may be an RFID reader (Radio Frequency Identification, RFID), and the RFID reader can read electronic label data, that is, the RFID reader. The identification part 6 comprises an identification coil, and the identification part 6 is provided at an outer side face or an inner side face of the housing 2. The identification part 6 is provided at an appropriate position of the surgical stapler according to actual use conditions, for example, the identification part 6 is provided at a rear end part or a top part or a side part of the surgical stapler.

The information identifier 10 may be installed on the front end, side or top of the staple cartridge assembly 9, which is not strictly limited in this embodiment. The information identifier 10 may be fixedly connected to the staple cartridge assembly 9, and may also be detachably connected, which is not strictly limited in this embodiment.

In this embodiment, only after the information label is successfully identified, the control part 17 can control the surgical stapler to be in an activated state, so that the surgical stapler can be normally used. In this way, it can be screened whether the staple cartridge assembly 9 complies with a using standard, so as to avoid installing the staple cartridge assembly 9 having a failure or other problems, thereby improving the safety of the operation.

Further, the control part 17 is also used for recording the total identification times and the total success identification times of the identification part 6, and acquiring a preset correspondence between the total identification times and the success identification times; determining a preset total identification success times according to the correspondence and the total identification times; and comparing the total identification success times with the preset total identification success times, and if the total identification success times are greater than or equal to the preset total identification success times, controlling the surgical stapler to be in a shutdown state.

The preset correspondence between the total identification times and the total identification success times may be a proportional relation, for example, the total identification times: the preset correspondence between the total identification times and the total identification success times=2:1. Certainly, other correspondence may also be adopted, which is not strictly limited in this embodiment.

Since the body of the surgical stapler (excluding parts of the staple cartridge assembly 9) may be used multiple times, the identification part 6 may identify a plurality of different staple cartridge assemblies 9. In this embodiment, the preset total identification success times are defined by the total identification times based on a preset correspondence between the total identification times and the total identification success times. In this way, the total identification success times may be limited. If the total identification success times are greater than or equal to the preset total identification success times, the surgical stapler is in a stopped state, i.e., a state incapable of being used, thus limiting the usage times of the main body of the surgical stapler, as a result, it is possible to avoid occurrence of a situation in which the main body of the surgical stapler are used too much and the surgical stapler tends to be broken down or bacteria are over the limit.

Further, the identification part 6 acquires an identification record of the information identifier 10 on the staple cartridge assembly 9, and if the identification record is a successfully identified record, it is determined that the identification of the information identifier 10 fails.

In this embodiment, if the staple cartridge assembly 9 has been successfully identified, this indicates that the staple cartridge assembly 9 may have been used, in which case the identification result of the identification part 6 still has failed, so as to avoid the situation in which the staple cartridge assembly 9 has been used repeatedly.

In addition, the surgical stapler of the present application further comprises a confirmation switch 14, a firing switch and a retraction switch. After the confirmation switch 14 is closed, a trigger 5 is pulled, the trigger 5 pushes a firing trigger link 12, the firing trigger link 12 triggers the firing switch, and a rack 8 can drive the firing lever to make a protrude action. When the trigger 5 is pushed up, the trigger 5 pushes the retraction trigger link 13, the retraction trigger link 13 triggers the retract switch, the rack 8 can drive the trigger lever to retract, and when the protrusion 11 of the rack 8 is located in the sensing area of the sense part, the drive part 4 stops running so as to terminate the firing operation. In this way, the operator can also manually operate, thereby improving the flexibility of use of the surgical stapler.

In a specific application, as shown in FIG. 6, the control part 17 comprises a processor 1701 (CPU), a power supply management part 1702 (PWM) and a memory 1703, in which the processor 1701 is respectively connected to the indication lamp 3, the drive part 4, the trigger 5 and the identification part 6, so as to specifically transmit and receive an input instruction and transmit a corresponding control signal, and for a specific control process, reference can be made to the description of the described embodiments, and the details will not be described herein again. The indication lamp 3 and the trigger 5 may be connected to the processor 1701 in a connection manner of programmable input output (PIO) to implement data transmission. The memory 1703 is configured to store transmitted data.

The battery management part 1702 is connected to the battery 102 via the battery circuit board 15, and the battery management part 1702 is used for monitoring the state of the battery 102, so as to prevent the battery 102 from working over-current or over-voltage.

According to a second aspect, an embodiment of the present invention provides a method for controlling a surgical stapler, which is applied to the foregoing surgical stapler and includes:

Step 101: Obtain a real-time drive current value and a jump current average value of a drive part 4.

Step 102: determining a difference value between the drive current value at the current moment and the drive current value at the previous moment.

Step 103: comparing the difference value with a jump current average value, and if the difference value is greater than the jump current average value, controlling the drive part 4 to stop working.

According to the control method for a surgical stapler provided in the embodiments of the present invention, the method comprises: acquiring a real-time drive current value and a jump current average value of a drive part 4; then determining a difference value between the drive current value at the current moment and the drive current value at the previous moment; and then comparing the difference value with the jump current average value, and if the difference value is greater than the jump current average value, controlling the drive part 4 to stop working. Thus, an operator does not have to determine by his or herself whether anastomosis action is completed before operating the surgical stapler, thereby increasing surgical efficiency.

Further, the method further comprises:

When the retraction trigger link or the firing trigger link is triggered, the drive part drives the firing lever to retract or advance.

The present invention has been described with reference to the above embodiments, but it should be understood that the above embodiments are for purposes of illustration and description only and are not intended to limit the present invention to the scope of the described embodiments. In addition, it should be understood by those skilled in the art that the present invention is not limited to the above embodiments, and various changes and modifications may be made according to the teachings of the present invention, and all such changes and modifications are within the scope of protection of the present invention. The scope of protection of the present invention is defined by the appended claims and their equivalents.

The invention claimed is:

1. A surgical stapler, wherein comprising a housing, a control part and a drive part for providing power are provided in the housing, and the control part is electrically connected to the drive part;
the control part is configured to acquire a real-time drive current value and a jump current average value of the drive part; determining a difference value between a drive current value at a current moment and a drive current value at a previous moment; and comparing the difference value with a jump current average value, and if the difference value is greater than the jump current average value, controlling the drive part to stop working.

2. The surgical stapler according to claim 1, wherein the control part is further configured to acquire a historical drive current value of the drive part; determining a difference value between the drive current values at two adjacent moments; and determining the jump current average value according to all the difference values.

3. The surgical stapler according to claim 1, wherein the control part is further configured to compare the real-time drive current value with a drive current threshold value, and when the real-time drive current value is greater than or equal to the drive current threshold value, controlling the drive part to stop working.

4. The surgical stapler according to claim 1, wherein the surgical stapler further comprises a transmission part and a firing lever; the drive part is connected to one end of the firing lever through the transmission part; the control part is electrically connected to the drive part;
the control part is used for controlling, when the surgical stapler is activated, the drive part to drive the firing lever through the transmission part to perform a reset calibration action.

5. The surgical stapler according to claim 4, wherein the surgical stapler further comprises a load switch and a detachable staple cartridge assembly; the control part is electrically connected to the load switch;
when the staple cartridge assembly is installed, the staple cartridge assembly triggers the load switch;
the control part is used for recording a trigger time of the load switch, and comparing the trigger time with a time threshold value, and if the trigger time is greater than or equal to the time threshold value, determining that staple cartridge assembly is loaded successfully.

6. The surgical stapler according to claim 5, wherein the control part is further configured to compare the real-time drive current value with a preset variable current value, when the real-time drive current value is greater than the preset variable current value, controlling the drive part to drive the firing lever to continue to move in a direction away from the drive part via the transmission part, so as to increase the closing stroke of the staple cartridge assembly and reduce the rotation speed of the drive part, so as to increase the tissue positioning capability of the staple cartridge assembly.

7. The surgical stapler according to claim 5, wherein the surgical stapler further comprises an identification part electrically connected to the control part, and the staple cartridge assembly is further provided with an information identifier;
the identification part is configured to identify an information identifier on the staple cartridge assembly;
and the control part is configured to control the surgical stapler to be in the stopped state if the identification fails, and to control the surgical stapler to be in the activated state if the identification succeeds.

8. The surgical stapler according to claim 7, wherein the control part is further configured to record total identification times and total identification success times of the identification part, and obtain a preset correspondence between the total identification times and the total identification success times; determining a preset total identification success times according to the correspondence and the total identification times; and comparing the total identification success times with the preset total identification success times, and if the total identification success times is greater than or equal to the preset total identification success times, controlling the surgical stapler to be in a shutdown state.

9. The surgical stapler according to claim 7, wherein the identification part acquires an identification record of the information identifier on the staple cartridge assembly, and if the identification record is a successful identification record, then determining the identification of the information identifier fails.

10. The surgical stapler according to claim 4, wherein the control part is further used for controlling the drive part to drive the firing lever through the transmission part to perform a reset calibration action when the staple cartridge assembly is removed.

11. The surgical stapler according to claim 4, wherein the surgical stapler further comprises a sense part disposed in the housing; the transmission part is provided with a protrusion, the sensing area of the sense part is located on a moving path of the protrusion on the transmission part, and the control part is electrically connected to the sense part;
the control part is used for controlling, when the surgical stapler is activated or the staple cartridge assembly is removed, the drive part to drive the firing lever to move in a direction close to the drive part via the transmission part, so that the sense part senses the protrusion for the first time;
when the sense part senses the protrusion for the first time, the drive part is controlled to drive the firing lever to move in a direction away from the drive part via the transmission part, so that the protrusion is detached from the sensing area of the sense part;
when the sensing area of the sense part is detached, controlling the drive part to drive the firing lever to move in a direction close to the drive part via the transmission part, so that the sense part senses the protrusion for a second time;
controlling the drive part to stop working when the sense part senses the protrusion for the second time.

12. The surgical stapler according to claim 4, further comprising a detachable power supply and a battery circuit board disposed inside the housing, the control part is electrically connected to the battery circuit board;

and the control part is configured to, when the power supply is installed, collect a voltage on the battery circuit board, determine whether the voltage is an operating voltage, and if the voltage is an operating voltage, determine that the surgical stapler is activated.

13. A method for controlling a surgical stapler, applied to the surgical stapler according to claim 1, comprising:

acquiring a real-time drive current value and a jump current average value of a drive part;

determining a difference value between a drive current value at a current moment and a drive current value at a previous moment;

comparing the difference value with a jump current average value, and if the difference value is greater than the jump current average value, controlling the drive part to stop working.

14. The control method according to claim 13, wherein the method further comprises:

when the retraction trigger link or the firing trigger link is triggered, the drive part drives the firing lever to retract or advance.

* * * * *